United States Patent [19]

Stokley et al.

[11] 4,167,117
[45] Sep. 11, 1979

[54] APPARATUS AND METHOD FOR SAMPLING FLOWING FLUIDS AND SLURRIES

[75] Inventors: Charles O. Stokley; Thomas W. Muecke; Clay Gruesbeck, Jr.; William M. Salathiel, all of Houston, Tex.

[73] Assignee: Exxon Production Research Company, Houston, Tex.

[21] Appl. No.: 922,909

[22] Filed: Jul. 10, 1978

[51] Int. Cl.² ............................................. G01N 1/20
[52] U.S. Cl. .................................................. 73/422 R
[58] Field of Search ....................... 73/422 R, 422 GC

[56] References Cited

U.S. PATENT DOCUMENTS

| 2,322,018 | 6/1943 | Huber | 73/422 R |
| 3,083,577 | 4/1963 | Nelson | 73/422 TC |
| 3,084,554 | 4/1963 | Perilloux | 73/422 TC |
| 3,090,323 | 5/1963 | Smith | 73/422 TC |
| 4,018,089 | 4/1977 | Dzula | 73/422 R |

Primary Examiner—S. Clement Swisher
Attorney, Agent, or Firm—Gary D. Lawson; Robert B. Martin

[57] ABSTRACT

A method and apparatus for sampling the composition of fluid flowing through a conduit which includes a sampling conduit having an inlet disposed within said conduit and transverse to the axis of fluid flow in said conduit and an outlet connected to said conduit downstream of said inlet, and means for measuring the composition of fluid flowing through the sampling conduit. The sampling conduit is sized in relation to the conduit to cause isokinetic withdrawal of fluid from said conduit into said sampling conduit.

9 Claims, 5 Drawing Figures

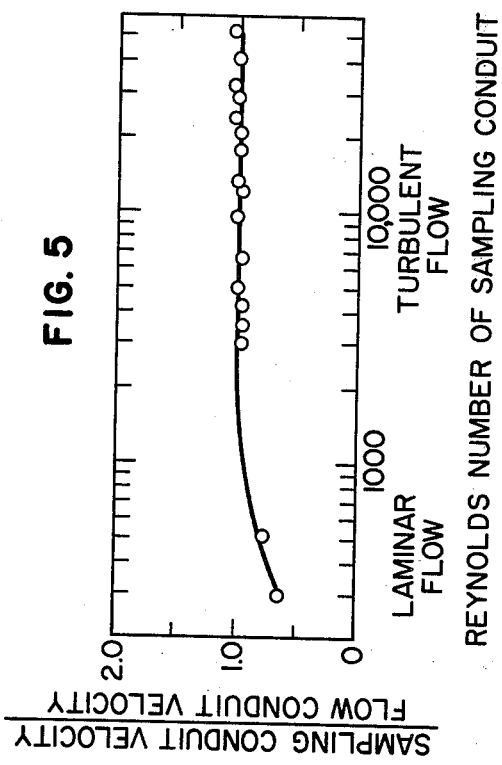
FIG. 5
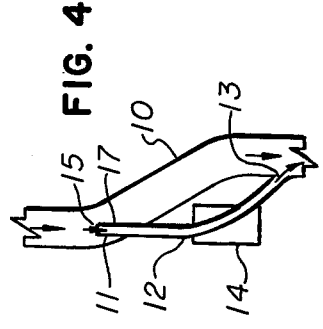
FIG. 4
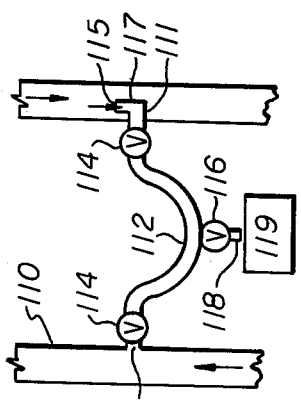
FIG. 2
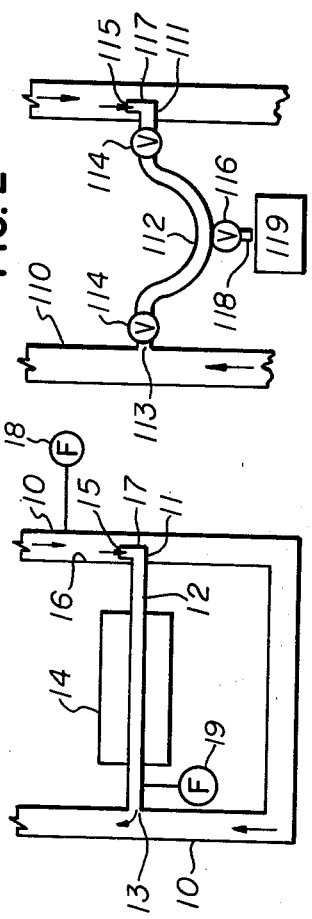
FIG. 3
FIG. 1

APPARATUS AND METHOD FOR SAMPLING FLOWING FLUIDS AND SLURRIES

BACKGROUND OF THE INVENTION

1. Field of the Invention

This invention relates to apparatus for obtaining samples of flowing fluid streams substantially identical in composition to the composition of the flowing streams.

2. Description of the Prior Art

In sampling flowing oil wells, reliable and accurate means of sampling is urgently needed to determine sand concentrations so that appropriate sand control techniques can be implemented when needed. Significant sand production is occurring in the newly developing areas of crude oil production. A means of sampling produced fluids to determine accurately and efficiently the amount of sand produced is currently unavailable. To compound the sampling problem, many oil wells are being produced at extremely high rates, i.e., 5,000 to 30,000 barrels (795 to 4,770 cubic meters) of oil per day. This complicates the technique of capturing representative samples of the flowing stream because it would be impractical to divert entire high velocity streams for short enough periods of time to obtain manageable size samples.

Securing true samples of sand entrained in a flowing fluid can be difficult. One problem is that any change in the kinematic conditions of the system will cause heavier and lighter particles in the fluid to flow along different paths depending on the pressure changes occuring along the different paths. Placing a sampling device in the flow stream is enough in itself to produce changes in the kinematic conditions of the system so that it becomes difficult or impossible to obtain a true and accurate sample of the material moving along the flow stream.

Another problem in obtaining representative samples of a well fluid containing solids is that stratification or irregular dispersal of the solid particles may occur in the kinematic system, hence a sample of only a portion of the stream may not necessarily be representative of the composition of the flow.

The inadequacy of sampling a flowing stream, particularly containing entrained solids such as sand, with a non-isokinetic sampling system has been recognized and attempts have been made to devise isokinetic systems; see for example, U.S. Pat. Nos. 3,473,388 issued Oct. 21, 1969 and 3,921,458 issued Nov. 25, 1975. A principal disadvantage with these isokinetic sampling devices is that outside pumping and instrumentation are necessary to establish isokinetic sampling.

A need exists for an improved apparatus and method for isokinetic sampling of flowing dispersions.

SUMMARY OF THE INVENTION

According to the present invention a sampling loop apparatus is provided for sampling the composition of fluid flowing through a fluid flow conduit comprising a sampling conduit having a first end disposed inside said fluid flow conduit and lying on a plane transverse to the path of the fluid flow in the flow conduit and having a second end connected to and communicating with said fluid flow conduit downstream of said first end, and a means for sampling fluid from the sample conduit. The sampling conduit is sized in relation to said fluid flow conduit to cause isokinetic withdrawal of fluid from said fluid flow conduit into said sampling conduit.

Preferably, the diameter of said fluid flow conduit between said first end and said second end of said sampling conduit is greater than the diameter of said sampling conduit. More preferably, both the length and diameter of the fluid flow conduit are larger than said sampling conduit.

The present invention provides means to produce the same or substantially the same average flow velocity at the inlet of the sampling conduit and at points upstream of the inlet in the undisturbed flow of the flow conduit. This flow velocity relationship may be obtained by adjusting the length and/or diameter of the fluid flow conduit or the sampling conduit between the points where the two conduits are in communication with each other. The diameter adjustment may be made at any point along the length of the conduits. For example, the diameter of the sample conduit or the fluid flow conduit may be adjusted only at the plane of sampling, hence the diameter of either conduit does not need to be uniform.

A practical means of obtaining isokinetic sampling is to adjust the length of one of the conduits without changing the diameter of either conduit. Another technique is to alter the roughness of either or both conduits, thereby changing the friction factor of said conduits.

The method of sampling using the present apparatus is also an aspect of the present invention.

An advantage of the present invention is the absence of any outside pump means to obtain an isokinetic sampling system. A particularly significant advantage is that isokinetic sampling is maintained over a broad range of fluid properties and flow conditions without recourse to appended servomechanical systems.

BRIEF DESCRIPTION OF THE DRAWINGS

FIG. 1 is a schematic representation of the present apparatus showing a sample conduit as a shunt across a loop of fluid flow conduit.

FIG. 2 is a schematic representation of one embodiment of the present invention.

FIG. 3 is a graph illustrating the effect of sampling velocity on sampling error of sand in water.

FIG. 4 is an alternate schematic embodiment of the apparatus of FIG. 1.

FIG. 5 is a graph illustrating the ability of one embodiment of this invention to maintain isokinetic sampling conditions over a broad range of operating conditions.

DESCRIPTION OF SPECIFIC EMBODIMENTS

The central feature of the present invention is an apparatus and method for obtaining a sample of a fluid from a fluid flow conduit in which the sample has the same composition as the fluid in the conduit. The manner of analyzing the fluid sample in the sampling conduit is not a primary concern of this invention. For example, physical samples of fluid may be recovered by providing two solenoid gates to close off a portion of the sampling conduit so that fluid can be drained into a collection vessel. This can be repeated at intervals to determine the composition of the fluid flowing through the fluid flow conduit for any given period of time.

A representative sample of a dispersion flowing through a flow conduit can only be obtained if the sample is withdrawn isokinetically, Isokinetic withdrawal or isokinetic sampling occurs when the fluid streamlines in and around the sampling conduit inlet are congruent with the streamlines describing the dispersed particle trajectories in and around the sampling conduit inlet. Such congruence of the fluid and particle streamlines may be further termed isokinetic flow. Isokinetic flow occurs only when the average fluid velocity at the sampling conduit inlet is equal to the average fluid velocity at points upstream of the inlet in the undisturbed flow of the flow conduit. If the average velocity of fluid withdrawal in the sampling conduit inlet is greater than the average fluid velocity in the upstream flow conduit, dispersed particle inertia will carry a disproportionate number of particles past the inlet while the fluid streamlines will converge into the inlet. A sample so obtained will contain a lower concentration of dispersed particles than the fluid in the flow conduit. Conversely, if the average fluid withdrawal velocity in the sampling conduit inlet is less than the average velocity in the upstream flow conduit, dispersed particle inertia will carry a disproportionate number of particles into the inlet as the fluid streamlines diverge past the inlet. A sample obtained in this way will contain a higher concentration of dispersed particles than the fluid in the flow conduit. The dispersed particles in question may be gas bubbles, liquids immiscible with the predominant fluid, or solids.

Isokinetic flow is obtained according to the present invention by adjusting the sampling inlet diameter, the fluid flow conduit diameter at the point of sampling, the two conduit lengths and the two conduit diameters. Isokinetic sampling by the present invention is insensitive to the velocity in the fluid flow conduit provided the flow in the sampling and flow conduits are both laminar or both turbulent. The size of the sample obtained in the sampling conduit may be first determined by sizing the sampling conduit to produce the desired sample volume and then, for example, adjusting the sampling inlet diameter and the fluid flow conduit length between the two ends of the sampling conduit to obtain the same flow in both conduits.

The relationships between the diameter and length of the conduits may be readily determined by trial and error, however, it is preferred to use suitable equations to approximate the appropriate relationships and then make the necessary adjustments to obtain the desired isokinetic flow. Because the characteristics of the flow regimes for turbulent and laminar flow are different, equations for any such regime must be developed separately.

One example of an equation to estimate the ratio of the length of the flow conduit and the length of the sampling conduit for pipe conduits having turbulent flow is given by $$\frac{L}{1} = \frac{D^{4.75}}{d^{1.25}\left[\frac{x^2 D^2}{y^2} - d^2\right]^{1.75}}$$ Equation 1 where:
L = the length of the fluid flow conduit between sampling conduit inlet and outlet
l = the length of the sampling conduit between the inlet and outlet
D = the diameter of the fluid flow conduit
d = the diameter of the sampling conduit
x = the ratio of the inside diameter of the sampling conduit to the inside diameter of the sampling inlet
y = the ratio of the inside diameter of the fluid flow conduit downstream of the sampling conduit inlet to the inside diameter of the fluid flow conduit at the inlet.

The above equation assumes the roughness characteristics of the conduits are negligible and that fluid flow is turbulent from a Reynold's number of 2500 to 100,000 where the pipe conduit Reynold's number is given by $(dv\rho)/\mu$ and
d = pipe diameter
v = fluid velocity
$\rho$ = fluid density, and
$\mu$ = fluid viscosity Various methods of analysis not requiring recovery of a sample from the sampling conduit may be employed, such as photometric, electrolytic and the like. For example, in determining density or specific gravity of a fluid, a density cell such as the CL-10TY series density cell available from Automation Products, Inc., Houston, Tex. may be used. These devices comprise a U-tube which is mechanically vibrated by an electric coil. The frequency of vibration becomes a function of the mass of the fluid. If the density of the fluid increases, the effective mass of the U-tube increases. By using a pick-up coil, the frequency of vibration can be sensed and converted to AC voltage which is a function of the density or specific gravity of the flowing fluid.

In a preferred embodiment, means is provided for capture of a sample in the sampling conduit. The term "capture" as used herein is understood to include physical capture or recovery of a sample and subsequent analysis and/or in situ conduit analysis or evaluation of the sample.

The present apparatus may be used to sample homogeneous and heterogeneous system of fluids, solids, gases, mixtures of fluids and solids, and mixtures of gases and liquids. The present apparatus has been found to be particularly useful for the sampling of liquids containing entrained particulate solids such as sand.

When the apparatus and method are employed with liquid-containing solids, a random dispersal of the solids in the fluid can be obtained if the fluid flow conduit is arranged to allow vertical downward flow of the fluid. This vertical arrangement provides, at least theoretically, a flow system from which a true representative sample may be taken by the sampling conduit. However, a horizontal system may be used if appropriate in-line mixing means are provided to obtain a similar random dispersion of solids.

FIG. 1 shows a schematic representation of the apparatus wherein the fluid flow path through fluid flow conduit 10 is shown by the arrow. A sampling conduit 12 has hollow probe 11 disposed inside conduit 10. The sampling conduit has an ingress or inlet end 15 and a outlet or egress end 13 communicating with said conduit 10 downstream of said inlet end 15. The fluid flow proceeds through conduit 10 and sampling conduit 12 and exits through outlet 13 back into conduit 10. Flow meters 18 and 19 are attached to conduits 10 and 12, respectively, to measure the flow rate in the conduits. A capture or analysis means, as described above, is illustrated by the numberal 14.

As shown in FIG. 1, the inlet 15 of probe 11 is positioned away from the wall 16 of conduit 10 in a plane perpendicular to the path of fluid flow. This positioning aligns the inlet 15 to capture fluid and minimizes the disturbance of the fluid at the point of sample entry into the sampling conduit 12. In the practice of this invention, inlet 15 should lie on a plane transverse to the flow path of fluid in conduit 10; this invention does not require that inlet 15 lie on a plane perpendicular to the path of fluid flow as generally shown in FIG. 1.

Although FIG. 1 shows the inlet end 15 approximately at the center of the conduit 10, it need not be at the center because the disturbance of the flow in conduit 10 caused by probe 11 occurs after the sample enters inlet 15. However, the inlet is preferably spaced away from the wall 16 to avoid any channeling effect that may occur along the wall.

The inlet 15 is located on an extension 17 of probe 11, this extension lies in the plane parallel to the longitudinal axis of fluid flow conduit 10.

The length of conduit 10 and sampling conduit 12 are adjusted as described above to obtain isokinetic sampling. It should be appreciated that the probe 11 and the extended portion 17 terminating in inlet 15 could be an arcuate shape and the same consideration discussed above regarding placement in conduit 10 would apply.

FIG. 2 illustrates one capture means wherein sampling conduit 112 extends into conduit 110 by use of probe 111 and extension 117. A fluid flows through conduit 110 and into inlet 115, into sample conduit 112, and hence through conduit 112 and outlet 113 into conduit 110 downstream of inlet 115. Located at each end or at any two points in sampling conduit 112 are two automatically operated valves 114 which when simultaneously activated trap the fluid in sampling conduit 112 therebetween. A third automatic valve 116 is located on line 118 which communicates with sampling conduit 112 through valve 116. Opening of valve 116 allows the sample in sampling circuit 112 to pass into collection vessel 119 via line 118. It should be appreciated that the valve 116 need not be automatically actuated. A relief valve (not shown) may also be provided to aid the flow out of conduit 112.

In one embodiment of this invention, a fluid flow is allowed to stabilize through conduit 110 and sampling conduit 112. Valves 114 are activated and immediately thereafter valve 116 is activated to drain the sample into vessel 119. The valve 116 is closed and valves 114 reopen and the steps above repeated. These steps may be conveniently preformed by a simple computer programmed to take samples at predetermined intervals.

FIG. 4 shows an apparatus, in schematic representation, which has the same elements and functionality as that in FIG. 1, however, the elements are arranged in a different spatial configuration. The same designations of these elements have been employed in both figures for that reason. In FIG. 4, the length of the fluid flow conduit 10 between the sampling conduit inlet 15 and outlet 13 is greater than the length of the sampling conduit 12.

Although the diameter of the fluid flow conduits and the diameter of the sample conduits in FIGS. 1, 2 and 4 are illustrated as being substantially uniform, it should be clear that this is not a requirement of the present invention. Variations in diameter are accounted for in the sample approximation equation set forth above and may be similarly accounted for in different systems by those persons skilled in the art.

The essential feature for the valid operation of the apparatus and method of this invention is that the fluid velocity be the same in the entrance of the sample conduit and in fluid flow conduit at the plane corresponding to the entrance of the sampling conduit. The variables which may be employed to obtain this result have been described and may be used in various combinations as those in the art will perceive and at the choice of those in the art.

To illustrate the advantage of isokinetic systems over non-isokinetic systems in actually determining the concentrations of solids in a system, laboratory tests were performed in which the flow velocities in the sampling conduit and flow conduit were varied. In FIG. 3, the error resulting from non-isokinetic flow is shown by plotting the relation between sampling velocity and pipeline velocity against the solids concentration in the sample versus true concentration of solids. The fluid solid mixture used consisted of 1% by weight sand in water wherein the sand varied in size from 80 to 120 mesh (the reference to mesh size is to the U.S. Standard Sieve Series).

An example of the performance of one embodiment of this invention is illustrated in FIG. 5. This apparatus was designed, assembled, and operated in the following manner.

A sampling device was designed to sample oil containing 0.2% by weight sand flowing through a 1½ inch (0.038/meter) inside diameter conduit at the rate of 1000 barrels (160 cubic meters) per day. The general configuration of the device is illustrated in FIG. 1.

The device was designed to sample the oil stream isokinetically using a 0.5 inch (1.27 centimeters) diameter sampling conduit in accordance to the following steps:

(a) The ratio of the length (L) of the fluid flow conduit between the inlet and outlet of the sampling conduit to the length (l) of the sampling conduit was calculated to be 3.2 in accordance with Equation 1 above where D=1.5 inches (3.81 centimeters) d=0.5 inch (1.27 centimeters) x=1.244 and y=1.0. This ratio was based on the assumption that both conduits were smooth and had a uniform diameter throughout their lengths.

(b) The sampling loop was constructed similar to the configuration in FIG. 1 using the L/l ratio determined in the first step (a). The sampling conduit length l was selected to be 3 feet (0.914 meters), therefore the length l of the flow conduit was constructed to be 9.6 feet (2.92 meters).

(c) Referring to the configuration in FIG. 1, the flow velocity in the fluid flow conduit 10 was measured using flowmeter 18 and simultaneously the velocity in the sampling conduit 12 was measured using flowmeter 19.

(d) The ratio of the lengths L/l was adjusted by removing a small section of sampling conduit so that the velocity as measured by flowmeters 18 and 19 were the same.

Tests were performed using this device which demonstrates the ability of this invention to maintain isokinetic sampling over a wide range of velocities and fluid properties. In a series of 17 tests in which the viscosity of the fluids was varied from 1.0 to 40 centipoises, the density of the fluid ranged from 0.86 grams/cubic centimeter to 1.0 gram/cubic centimeter, and the velocity of the fluid in the sampling conduit varied from 5 to 15 ft/sec (1.524 to 4.57 m/sec). The result of these tests, shown in FIG. 5 is that the ratio of the velocity in the sampling conduit to the fluid conduit was equal to 1.0 over the range of Reynolds number from 4,000 to 60,000. These tests also illustrate the necessity of maintaining either laminar or turbulent flow in both the flow conduit and the sampling conduit when one desires isokinetic sampling with such a device to be insensitive to velocity changes. As FIG. 5 shows, for sampling conduit Reynolds number below about 2000, the sampling process becomes progressively less isokinetic. This is largely due to the flow in the sampling conduit becoming laminar.

The principle of the invention and the best mode in which it is contemplated to apply that principle have been described. It is to be understood that the foregoing is illustrative only and that other means and techniques can be employed without departing from the true scope of the invention defined in the claims.

We claim:

1. An apparatus for sampling the composition of fluid flowing through a fluid flow conduit comprising:
   (a) a sampling conduit having an inlet disposed within said fluid flow conduit transverse to the axis of fluid flow in said fluid flow conduit and an outlet connected to said fluid flow conduit downstream of said inlet; and
   (b) means for measuring the composition of fluid flowing through said sampling conduit, said fluid flow conduit having a length and diameter greater than the length and diameter of said sampling conduit to cause isokinetic withdrawal of fluid from said fluid flow conduit into said sampling conduit.

2. The apparatus as defined in claim 1 wherein said means for measuring the composition of said fluid provides for removal of a fluid sample from said sampling conduit.

3. The apparatus as defined in claim 1 wherein said measuring means provides for in situ evaluation of a fluid sample in said sampling conduit.

4. The apparatus as defined in claim 1 wherein said sample conduit and said fluid flow conduit between said inlet and outlet of said sample conduit are uniform diameter.

5. The apparatus as defined in claim 1 wherein said sample conduit has a non-uniform diameter.

6. The apparatus as defined in claim 1 wherein said inlet of said sampling conduit lies on a plane substantially perpendicular to the axis of fluid flow in said fluid flow conduit.

7. The apparatus according to claim 1 wherein said fluid flow conduit has non-uniform diameter between said inlet and said outlet of said fluid sample conduit.

8. An apparatus for sampling the composition of fluid flowing through a conduit comprising:
   (a) a sampling conduit having an inlet disposed within said fluid conduit and an outlet connected to said fluid flow conduit downstream of said inlet; and
   (b) means for measuring the composition of fluid flowing through said sampling conduit, said fluid flow conduit having a length and diameter greater than the length and diameter of said sampling conduit to produce fluid flow within said inlet opening of said sampling conduit which has a velocity substantially equal to the average velocity of undisturbed fluid flow within said fluid conduit at a point upstream of said inlet opening.

9. The apparatus as defined in claim 8 wherein said means for measuring the composition of said fluid provides for removal of a fluid sample from said sampling conduit.

* * * * *